United States Patent
Sherman et al.

(10) Patent No.: US 7,833,203 B2
(45) Date of Patent: Nov. 16, 2010

(54) CATHETER SHAFT WITH UNDULATING SURFACE FOR REDUCED FRICTION

(75) Inventors: Darren R. Sherman, Ft. Lauderdale, FL (US); Robert Slazas, Miami, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 929 days.

(21) Appl. No.: 11/095,265

(22) Filed: Mar. 31, 2005

(65) Prior Publication Data

US 2006/0229574 A1 Oct. 12, 2006

(51) Int. Cl.
*A61M 5/00* (2006.01)

(52) U.S. Cl. .................... 604/264; 600/139

(58) Field of Classification Search .............. 606/1, 606/191–198, 159; 604/96.01–103.01, 104, 604/523–527, 264; 264/209.2, 313; 623/1.11, 623/1.12, 1.15; 600/374, 139
See application file for complete search history.

(56) References Cited

U.S. PATENT DOCUMENTS

| | | | | |
|---|---|---|---|---|
| 3,970,090 A | * | 7/1976 | Loiacono | 604/104 |
| 5,125,909 A | * | 6/1992 | Heimberger | 604/264 |
| 5,358,493 A | * | 10/1994 | Schweich et al. | 604/264 |
| 5,431,637 A | * | 7/1995 | Okada et al. | 604/264 |
| 5,827,304 A | * | 10/1998 | Hart | 606/159 |
| 5,885,508 A | | 3/1999 | Ishida | |
| 5,891,027 A | * | 4/1999 | Tu et al. | 600/374 |
| 5,938,587 A | * | 8/1999 | Taylor et al. | 600/139 |
| 6,648,874 B2 | * | 11/2003 | Parisi et al. | 604/525 |
| 6,786,889 B1 | * | 9/2004 | Musbach et al. | 604/103.1 |
| 7,316,709 B2 | * | 1/2008 | Limon | 623/1.11 |
| 2001/0056224 A1 | | 12/2001 | Renner et al. | |

FOREIGN PATENT DOCUMENTS

EP 1597999 A1 11/2005
EP 1652545 A1 5/2006

OTHER PUBLICATIONS

Dover®—Intermittent Female Catheter with a Matte Finish (2 pgs.).

* cited by examiner

*Primary Examiner*—Kevin T Truong
(74) *Attorney, Agent, or Firm*—George H. Gerstman; Seyfarth Shaw LLP

(57) ABSTRACT

A vascular catheter which comprises a catheter shaft, said catheter defining a first surface which is of undulating shape with a plurality of curved peaks, said peaks being spaced so that a second surface in contact with the first surface is spaced from at least a substantial portion of the first surface, to reduce friction of the catheter.

5 Claims, 5 Drawing Sheets

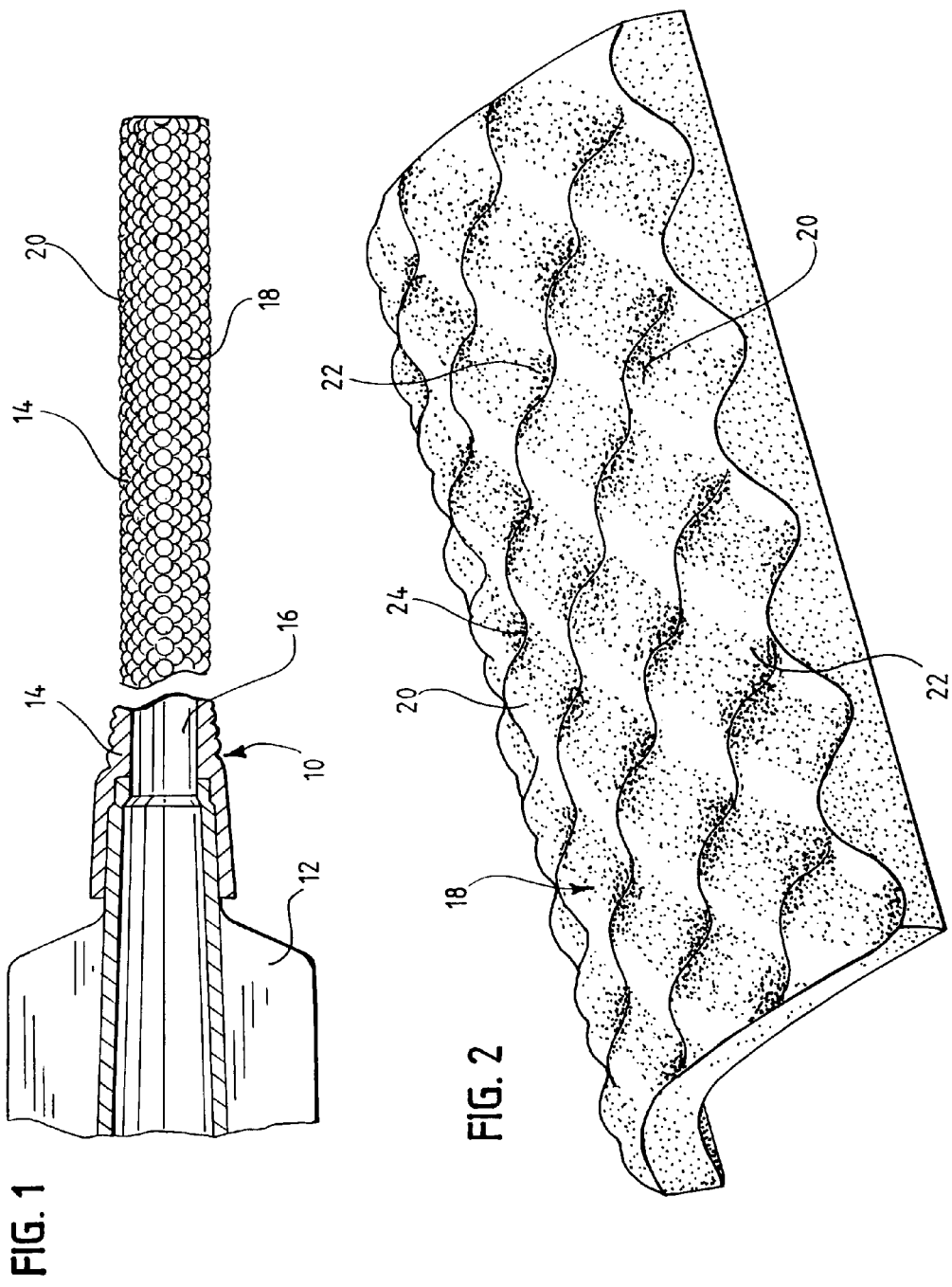

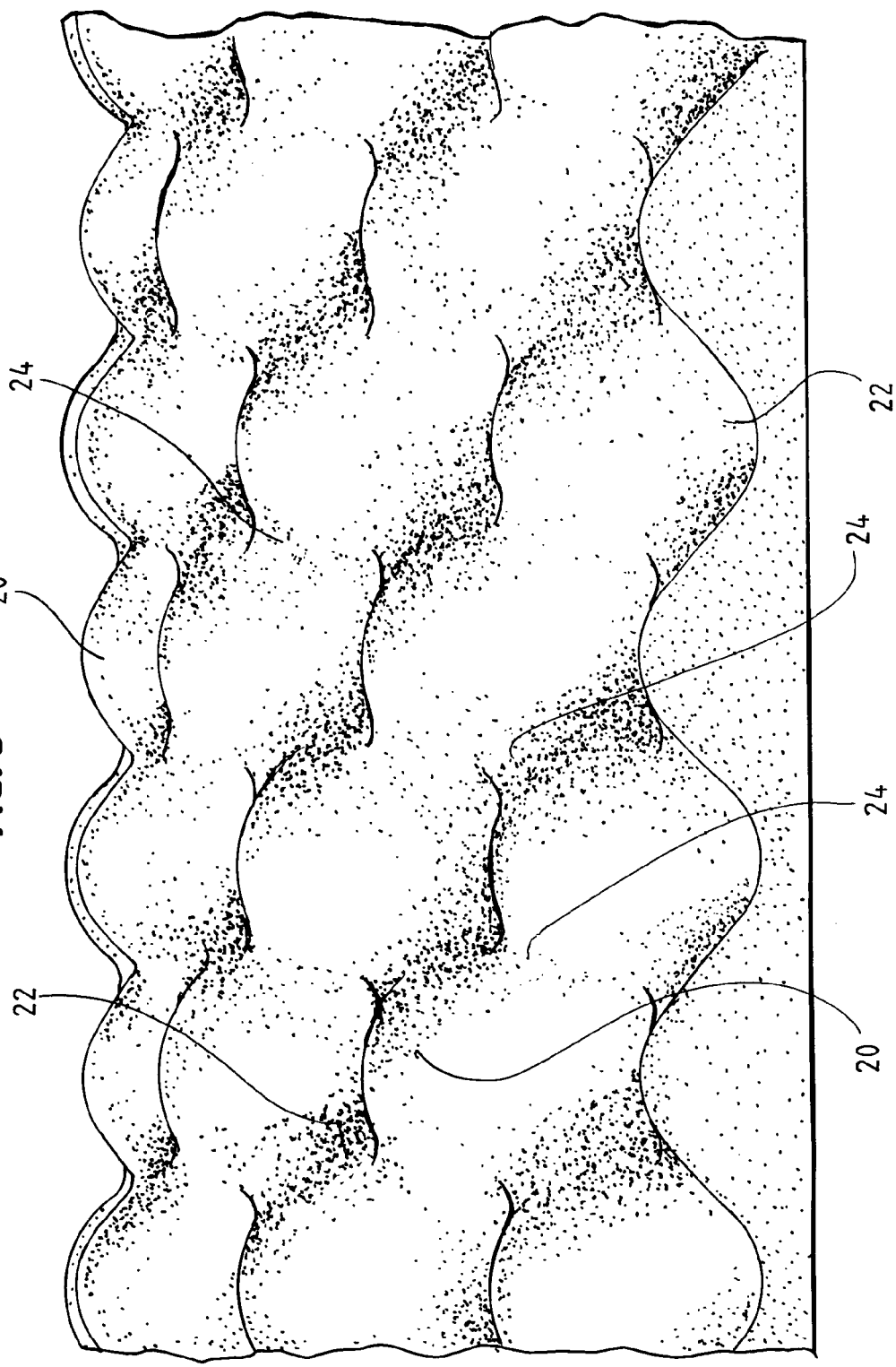

CATHETER SHAFT WITH UNDULATING SURFACE FOR REDUCED FRICTION

BACKGROUND OF THE INVENTION

Vascular catheters are known and in use for a variety of medical purposes. Basically, a catheter shaft is attached to a hub or other connector, and is inserted into the vascular system of the patient. Also, a guidewire or another catheter or stylet may pass through the lumen of a vascular catheter.

When positioning and moving a catheter, lower resistance to movement is desirable, either on its outer surface or at a lumen wall. In the prior art, many of the vascular catheters have been made smooth (slick and slippery) to accomplish this. However, in some circumstances, a smooth or slick surface can actually have higher frictional resistance, depending upon the surface against which it slides.

Other catheters, such as some disclosed in Waksman et al. U.S. Pat. No. 6,306,074 D1 are provided with a matte finish to reduce friction.

In accordance with this invention, an improved catheter, having reduced friction to tissues and other devices as it is advanced into the vascular system of a patient, is provided, exhibiting improvements over the prior art, and having less need for an added, lubricious coating, which can reduce the physician's manual control of the catheter.

DESCRIPTION OF THE INVENTION

In accordance with this invention, a vascular catheter is provided which comprises a catheter shaft, the catheter defining a first surface, for example, the outer surface of the catheter shaft. The first surface is of undulating shape, with a plurality of curved peaks, generally free of sharp edges. The peaks are spaced apart by a distance so that a second surface in contact with the peaks of the first surface is spaced from at least a substantial portion of the first surface area that does not comprise peaks. While not wishing to be limited by theory, it is believed that while the localized friction force felt at the peaks may increase compared with an unmodified surface, the total friction effect over the whole surface is reduced because of the areas that are free from sliding contact. The effect of this is to reduce the friction of the catheter as it slides along that second surface. The amount of friction reduction can thus be adjusted by the spacing of the peaks, which controls the amount of second surface that is so spaced.

While the first surface may be an outer surface, it may also, or in the alternative, comprise a similar, undulating surface along the wall of a catheter lumen, or a plurality of catheter lumens, if desired.

In some embodiments, the undulating shape comprises curved peaks, and corresponding valleys extending from peak to peak. In other embodiments, the undulating shape may comprise a plurality of curved peaks, substantially without valleys, or with valleys that are minimal and smaller, with a depth that is less than the height of the peaks, and not necessarily fully extending from peak to peak.

In some embodiments, the peaks are generally spaced apart by 0.005 mm. to 3 mm., preferably 0.01 to 2 mm, as measured from center to center of the peaks. In some embodiments, the peak height may be generally from 0.005 mm. to 1 mm., preferably 0.01 to 0.8 mm, measured from the normal, outer diameter of the catheter (i.e., that outer diameter that the catheter would exhibit if it had been extruded with a smooth surface without forming of the peaks, or prior to forming of the peaks with a die after extrusion). This height may be less than the peak to valley height. In some processes of manufacturing the undulating, smoothly curved surface in accordance with this invention some of the catheter material is laterally moved and piled to form the peaks, being taken from the valley areas.

Thus, the first surface of the catheter may define rounded, undulating peaks and valleys, in which the valleys generally extend between the peaks. Alternatively, the first surface may define spaced peaks, largely without valleys that extend from peak to peak. In some embodiments, the peaks may be adjacent to valleys which may surround the peak, or be just on a side thereof, and which do not extend from peak to peak. Unmodified catheter wall areas may exist on the outer diameter surface (and/or the inner diameter surface) in those circumstances where the peaks are widely separated. The peaks may be regularly arranged as in a grid or matrix, or irregularly arranged.

As stated, the undulating surface may be formed on the catheter after extrusion thereof by use of an appropriate shaping die, such as a knurling die. However, it is also possible for a catheter undulating surface to be directly extruded, as can be accomplished with proper selection of a plastic catheter extrusion material, in combination with the selection of a melt temperature and an extrusion speed which causes rounded lumps or peaks to form on the surface of the catheter. This is a matter of conventional technology for those skilled in the art of tube extrusion, and, prior to this invention, it is been a condition to be generally avoided rather than sought, as in this invention.

A catheter so modified may comprise a catheter that goes into a catheter introducer (which also is a catheter) with reduced friction. The outer catheter surface and/or the inner catheter surface may be of undulating shape as described. Such catheters may be of conventional materials such as PTFE or nylon.

DESCRIPTION OF THE DRAWINGS

In the drawings, FIG. 1 is an elevational, enlarged view of a vascular catheter in accordance with this invention, with a portion broken away and taken in section.

FIG. 2 is an enlarged, perspective view of a cut-away portion of the wall of the catheter tube, showing the outer surface.

FIG. 3 is a further enlarged, perspective view of the catheter wall of FIG. 2.

DESCRIPTION OF THE SPECIFIC EMBODIMENTS

Figure 4:
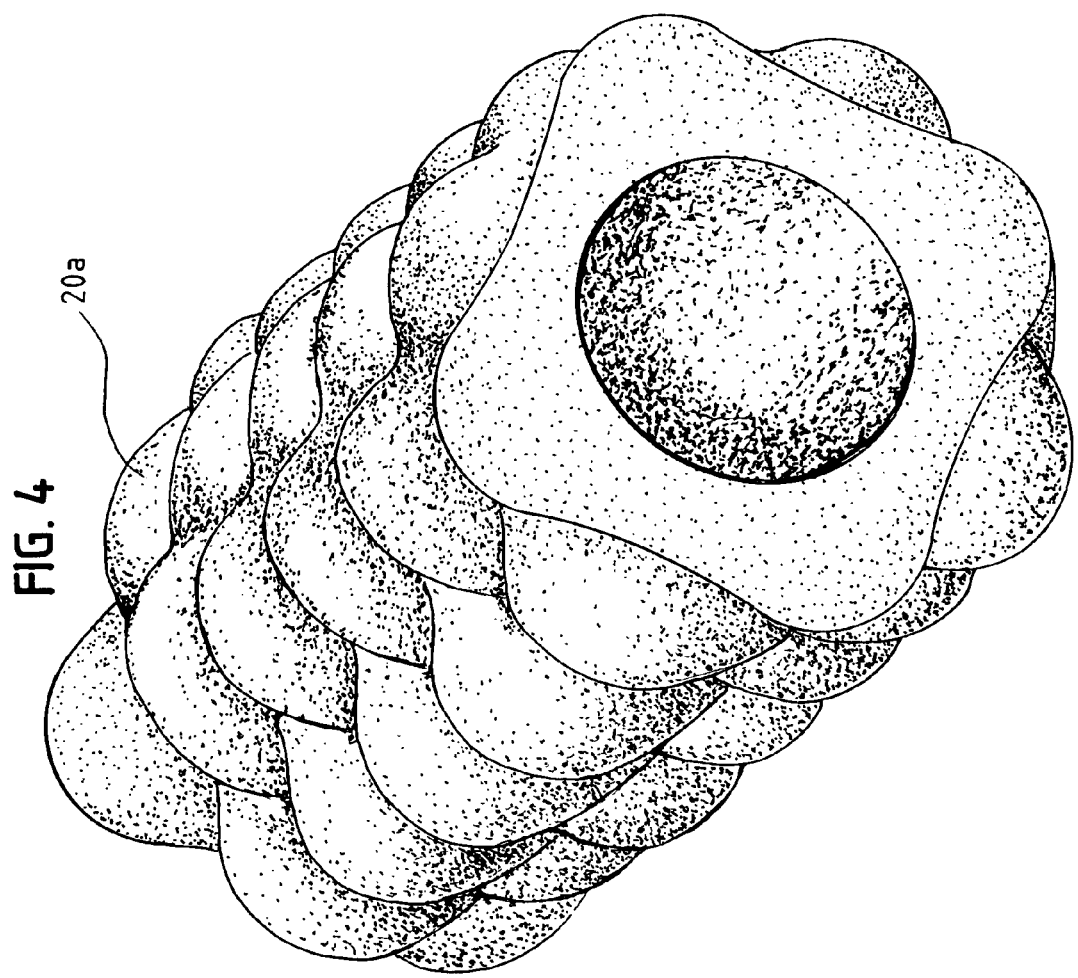
FIGS. 4-6 are enlarged, perspective views of the outer surfaces of other catheters in accordance with this invention, the catheter lumens are not being shown.

Referring to the drawings, intravascular catheter 10 comprises a hub, which is attached at one end in conventional manner to a catheter tube 14. Catheter tube 14 defines a lumen 16 and an outer surface 18, this surface 18 defining the first surface, which is of undulating shape, having a plurality of curved peaks 20, as shown in FIGS. 2 and 3. Valleys 22 are also found adjacent to curved peaks 20, the result being that the peaks are spaced so that a second surface such as the blood vessel wall, or a catheter introducer, that may surround the vascular catheter as it is being advanced, is spaced from at least a substantial portion of valleys 22, the effect of this being a reduction in friction, since the total surface area of outer catheter surface 18 which is in frictional contact with the blood vessel wall or catheter introducer is reduced.

It can be seen that peaks 20 do not have to be completely surrounded by valleys 22, as shown by FIGS. 1 and 2. Rather, in this embodiment, peaks 20 are rather like a mountain range having valleys 22 next to them, but being connected to adjacent peaks through what might be called a mountain pass or a lesser valley 24. The exact geometry of the undulating, rounded peaks 20 is not critical to obtain excellent friction reduction characteristics.

In another embodiment, the height of peaks or bumps of outer surface 18 of a catheter may extend approximately 23 microns over the normal, theoretical outer diameter of the catheter as indicated by the orifice of the extrusion die and the extrusion conditions. In the same embodiment, the centers of peaks are spaced apart by about 534 microns, on average, and the valleys generally represent depressed rings around the peaks, being the major source of the material from which the peaks are made. These valleys do not extend completely from peak to peak and typically have a maximum depth of about 10 microns from the theoretical catheter outer diameter. The catheter outer surface is an undulating, rounded surface, but with areas of unmodified catheter outer surface, because of the wider spacing of the peaks. In this embodiment, the catheter was extruded to directly obtain the outer, undulating surface 18, using a Pebax® nylon molding compound having a Durometer of Shore 55D.

FIG. 4 shows a catheter outer surface having undulating peaks 20a of differing heights.

Figure 5:
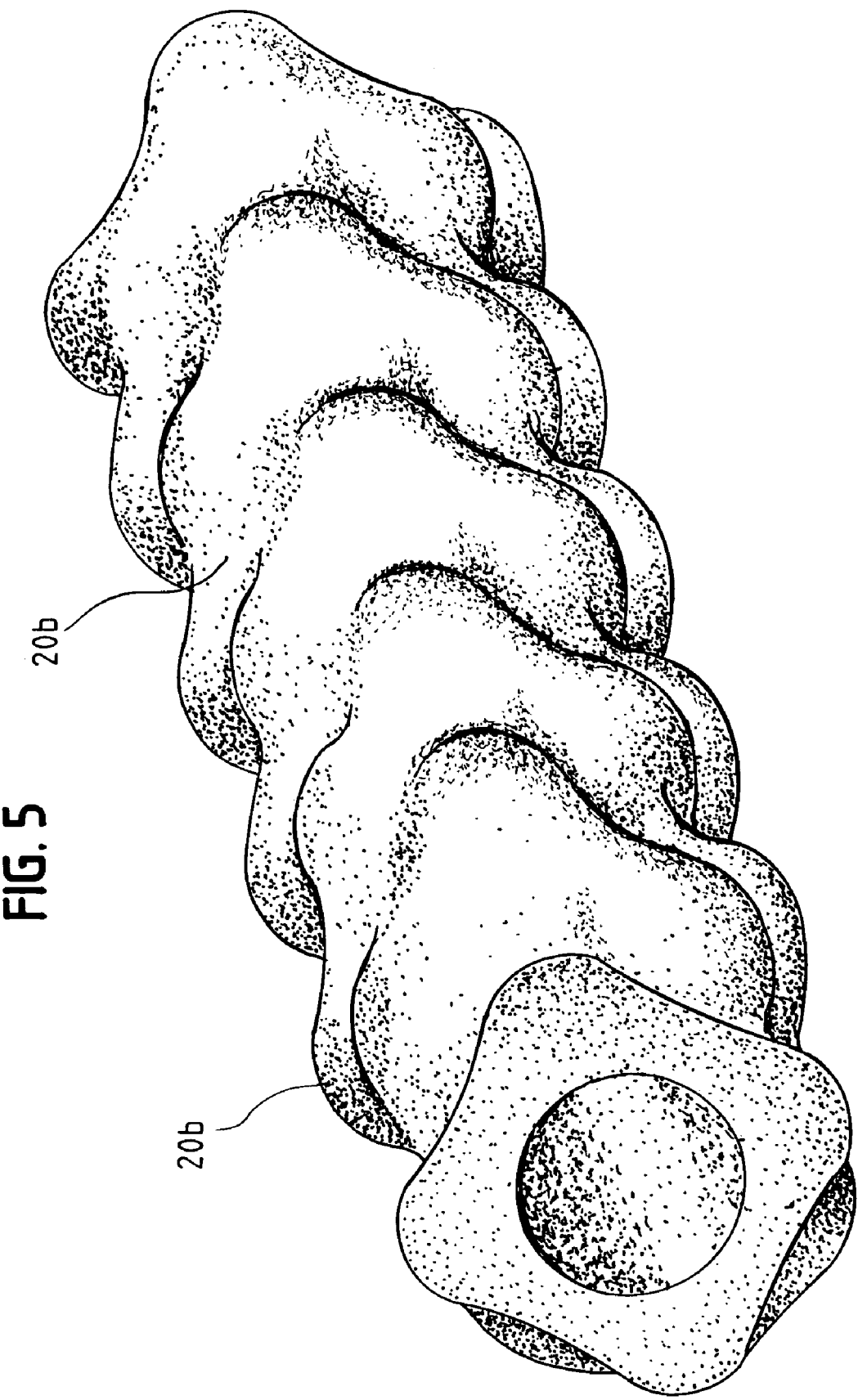

FIG. 5 shows a catheter outer surface having peaks 20b that are substantially transversely elongated.

Figure 6:
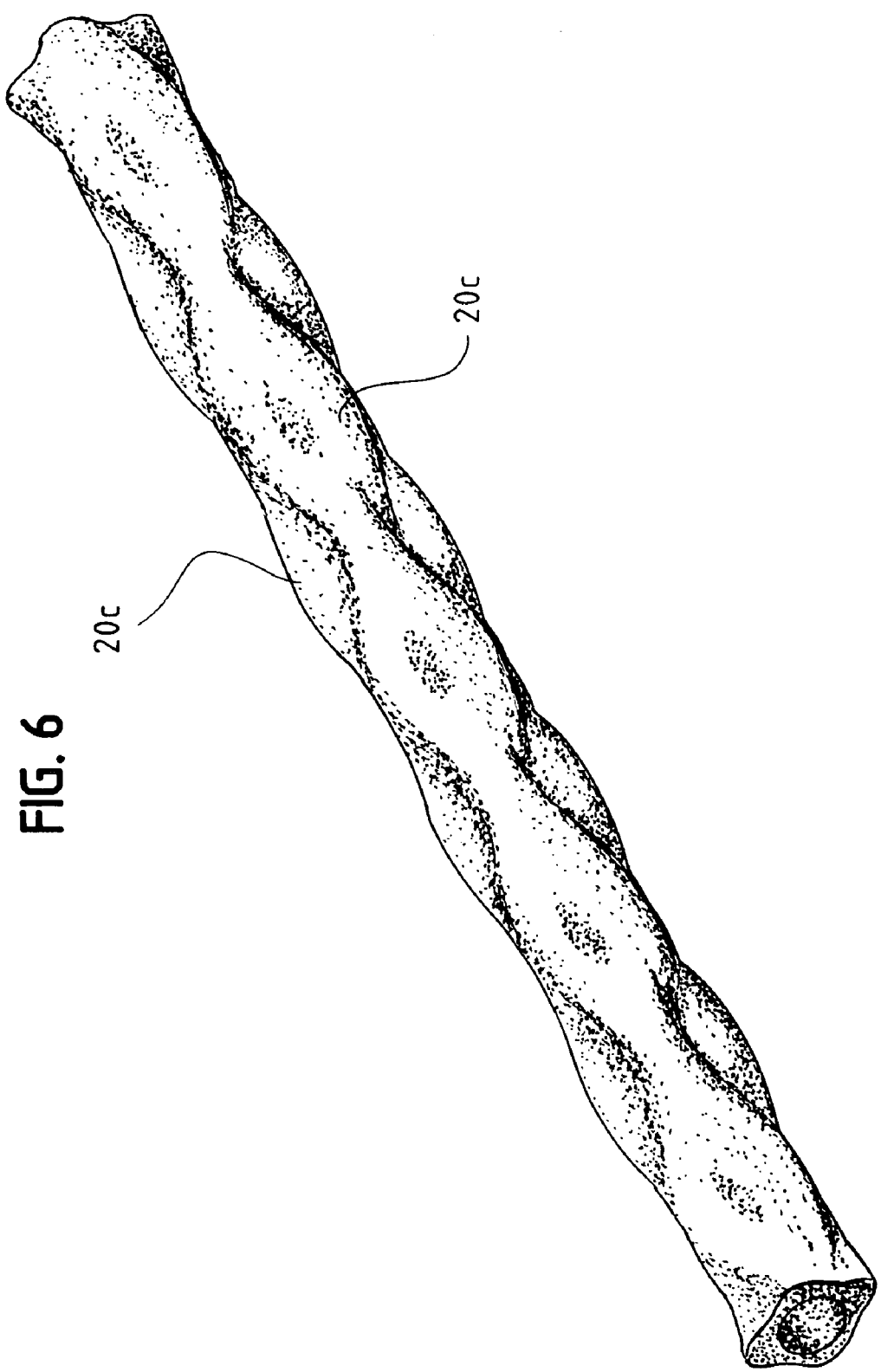

FIG. 6 shows a catheter outer surface having peaks 20c that are substantially longitudinally elongated.

The above has been offered for illustrative purposes only, and is not intended to limit the scope of the invention of this application, which is as defined in the claims below.

That which is claimed is:

1. A vascular catheter which comprises a tubular catheter shaft, said catheter shaft defining a friction-reducing outer surface which is of undulating shape;
   said outer surface having a plurality of curved peaks, deep valleys and lesser valleys;
   said peaks being connected to adjacent peaks by said lesser valleys;
   said deep valleys defining areas between adjacent peaks;
   said peaks being spaced so that a second surface in contact with the friction-reducing outer surface becomes spaced from said deep valleys and said lesser valleys.

2. The catheter of claim 1 in which said peaks are generally spaced apart by 0.005 mm. to 3 mm., measured from center to center of the peaks.

3. The catheter of claim 1 in which the peak heights are generally from 0.005 mm. to 1 mm.

4. The catheter of claim 1 in which said peaks are generally spaced apart by 0.01 mm. to 2 mm., measured from center to center of the peaks.

5. The catheter of claim 4 in which the peak heights are generally from 0.01 mm. to 0.8 mm.

\* \* \* \* \*